United States Patent [19]

Wright, II et al.

[11] Patent Number: 5,014,693
[45] Date of Patent: May 14, 1991

[54] CEILING-MOUNTED GAS DELIVERING UNIT FOR USE IN A CATHETER LABORATORY

[75] Inventors: William B. Wright, II, Katy; Dean D. Sauberli, Houston, both of Tex.

[73] Assignee: St. Luke's Episcopal Hospital, Houston, Tex.

[21] Appl. No.: 427,866

[22] Filed: Oct. 25, 1989

[51] Int. Cl.$^5$ ............................................. A61M 39/00
[52] U.S. Cl. ........................... 128/204.18; 128/203.12; 248/324; 248/280.1
[58] Field of Search ....................... 128/204.18, 205.11, 128/203.12; 248/324, 325, 330.1, 280.1

[56] References Cited

U.S. PATENT DOCUMENTS

| | | | |
|---|---|---|---|
| 3,981,340 | 9/1976 | Anderson et al. | 248/324 |
| 4,554,916 | 11/1985 | Watt | 128/203.12 |
| 4,863,133 | 9/1989 | Bonnell | 248/280.1 |
| 4,901,967 | 2/1990 | Petre | 248/327 |

OTHER PUBLICATIONS

Medrad, Inc., "The Medrad Overhead Counterpoise", Nov. 1987.
Siemens Aktiengesellschaft, "Universal Ceiling Stand 800/Universal Ceiling Stand 810", E325.

Primary Examiner—Edgar S. Burr
Assistant Examiner—Eric P. Raciti
Attorney, Agent, or Firm—Arnold, White & Durkee

[57] ABSTRACT

A low-bulk gas delivering apparatus for use in a catheter laboratory is provided. The apparatus includes a universally articulatable support arm, one end of which is adapted to mount onto a ceiling and the other end of which is mounted to a gas module. The gas module is adapted to deliver gas received from a hose which connects the gas module to a source of gas. The hose generally extends along the support arm and is disposed outside of the support arm. Therefore, the support arm is lighter, slimmer, and less bulky than previously used support arms.

41 Claims, 2 Drawing Sheets

CEILING-MOUNTED GAS DELIVERING UNIT FOR USE IN A CATHETER LABORATORY

BACKGROUND OF THE INVENTION

1. Field of the Invention

This invention relates generally to gas modules, and more particularly to a gas module which is especially adapted for use in a catheter laboratory.

2. Description of the Related Art

In the field of health care, it is often necessary or advantageous to administer one or more different types of gases to a patient. For instance, oxygen or air is administered to many patients to help them breath normally, and patients undergoing surgery are typically anesthetized using an anesthetic gas, such as nitrous oxide. Frequently, a patient undergoing surgery will receive oxygen and an anesthetic gas concurrently. In addition, during surgery, the surgeon often uses compressed air to remove fluids from internal organs, and a vacuum to extract fluids from the operating area.

In view of the advantageous use of these various gases, it is common to route various types of gases to a common delivery unit, which is often called a gas module. Gas modules include a plurality of outlets which are used to deliver the gases, and the outlets usually include regulating valves which adjust the pressure or flow of the gas being delivered to the patient. A gas module conveniently allows a hospital attendant to select a particular type of gas for administration to a patient, and to regulate the amount of ga delivered to the patient.

In many modern hospitals, a network of gas pipes runs throughout the hospital to deliver the various gases to the rooms in which they are needed. For instance, operating rooms typically receive oxygen, air, compressed air, vacuum, nitrogen, and anesthesia. In operating rooms, it is advantageous that the gas module is moveable, because different surgical operations require different numbers of surgeons to be in different positions within the operating room. Therefore, a gas module which may be located in a convenient location within the operating room prevents the gas module from being an obstruction, while it allows hospital personnel to effectively use the gas module.

While all of these different types of gases may be useful at one time or another in an operating room, all of these gases are not necessary in patients' individual rooms. However, since some patients require the administration of oxygen or air, pipes running within the walls or the ceilings of the hospital, deliver these two gases into the patients' rooms via wall or ceiling outlets. These rooms are typically arranged in a manner which is not subject to change. Therefore, to efficiently utilize the space, the gas modules are mounted on or in one of the walls of the room. The primary disadvantage of these wall mounted units is that they cannot be easily relocated.

As previously mentioned, moveable gas modules are preferred for use in examination rooms and operating rooms. Unfortunately, gas modules which receive gas from pipes running within the hospital ceiling or walls typically have a very limited range of motion. Commercially available ceiling-mounted gas modules are supported by bulky arms which have gas-carrying hoses running therethrough, and typically weigh over 500 pounds. The bulkiness and heaviness restricts the length and articulation of the arms, thus preventing the gas module from being conveniently positioned. Furthermore, the weight of the arms often prohibits manual operation and instead requires mechanical or electrical assistance.

Moreover, these ceiling-mounted gas modules cannot be used efficiently in examination rooms which contain a plurality of devices mounted above the examination table. In catheter laboratories, for instance, two X-ray tubes having opposed image intensifiers are used to produce two-dimensional images of a patient's internal organs. Each X-ray tube and its associated image intensifier is mounted onto a respective positionable U-shaped member so that an operator can accurately position each of the tubes and intensifiers about a patient. One of these U-shaped members, such as a LARC, positions one X-ray tube and image intensifier on either side of a patient. The LARC slides along the length of an examination table on two parallel tracks attached to the ceiling. The other of these U-shaped members, such as a Poly-C, positions the other X-ray tube and image intensifier above and below a patient, respectively. The Poly-C has two parallel arms that move the length of the examination table, and its base is attached to the floor. After considerable processing, the images produced by the image intensifiers are sent to monitors which are mounted on the ceiling on two parallel tracks which extend across the examination table, generally perpendicular to the LARC's tracks. Moreover, a physiologic monitor is also mounted above the examination table to relay the patient's vital statistics to the physician, as is, of course, a surgical light. Therefore, there is no room to mount a gas module on the ceiling above the examination table.

In rooms such as these, the ceiling mount of the gas module would have to be located away from the examination table because there is no room for the mount above the table. Therefore, the ceiling-mounted gas module must have a long reach so that it can be positioned reasonably near a patient. However, length is not the only concern. A ceiling-mounted gas module having long, bulky support arms cannot be easily positioned between the other devices in the room.

Due to the poor maneuverability, bulkiness, and restricted reach of commercially available ceiling-mounted gas modules, floor standing gas modules are typically used in crowded examination rooms and laboratories. The floor standing gas modules which receive gas from the network of pipes typically require long hoses which extend between the wall and the gas module. These hoses limit the range of motion of floor standing gas modules, and obstruct a large amount of the floor space in an examination room. Thus, they are not well suited for use in a crowded room. Many floor standing gas modules, however, use gas stored in tanks that are carried on the module. While these types of gas modules move on rollers, and therefore have a greater range of motion than the previously described floor standing models, they are quite heavy and large due to the tanks of gas which must be carried with the gas module. An additional problem stems from the fact that floor standing units are quite susceptible to contamination by dirt and fluids.

Accordingly, the prior art has various drawbacks and disadvantages.

SUMMARY OF THE INVENTION

The present invention overcomes many of these drawbacks and disadvantages by providing a low-bulk gas delivering apparatus for use in a catheter laboratory. The apparatus includes a universally articulatable support arm, one end of which is adapted to mount onto a ceiling and the other end of which is mounted to a gas module. The gas module is adapted to deliver gas received from a hose which connects the gas module to a source of gas. The hose generally extends along the support arm and is disposed outside of the support arm. Therefore, the support arm is lighter, slimmer, and less bulky than previously used support arms.

In accordance with a more specific aspect of the present invention, a ceiling-mounted gas delivering apparatus for use in a catheter laboratory is provided where the articulatable support member includes: a first support arm having a first end and a second end, the first end being adapted to attach to the ceiling so that the support arm extends downwardly from the ceiling toward the floor and is generally perpendicular to the floor; a second support arm having a first end and a second end, the first end of the second support arm being pivotally connected to the second end of the first support arm to permit the second support arm to pivot horizontally about the first support arm; and a third support arm having a first end and a second end, the first end of the third support arm being pivotally connected to the second end of the second support arm to permit the second end of the third support arm to move vertically upwardly toward the ceiling and downwardly away from the ceiling and to permit the third support arm to pivot horizontally about the second end of the second support arm. A gas module is rotatably mounted onto the second end of the third support arm, and a hose connects the gas module to a source of gas. The hose generally extends along the support member and is disposed outside of the support member.

Preferably, the articulatable support member is manually positionable, and is fully moveable throughout its range of motion by manually moving the gas module. Moreover, a self-leveling linkage which connects the gas module to the second end of the third support arm maintains a selected orientation of the gas module throughout the range of motion of the articulatable support member.

By supporting a gas module from a universally articulatable support arm, providing the support arm with at least two pivotable interconnections which enable the gas module to be moved horizontally and vertically, and providing a hose exterior to the support arm and which supplies gas from a source to the gas module, the gas module is adapted to be positioned around a patient.

BRIEF DESCRIPTION OF THE DRAWINGS

Other advantages of the invention will become apparent upon reading the following detailed description and upon reference to the drawings in which.

Figure 1:
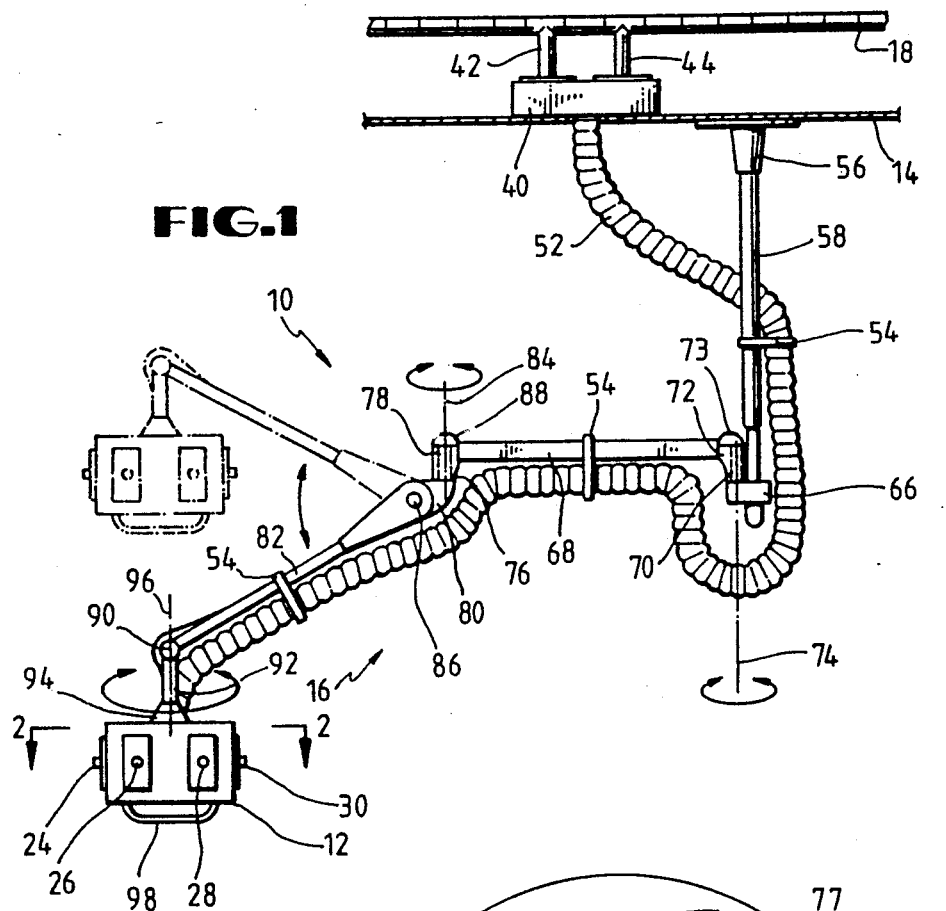
FIG. 1 is a side view of a ceiling-mounted gas delivering unit in accordance with the present invention.

While the invention is susceptible to various modifications and alternative forms, specific embodiments thereof have been shown by way of example in the drawings and will be described in detail herein. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Turning now to the drawings and referring initially to FIG. 1, a ceiling-mounted gas delivering unit is generally designated by a reference numeral 10. The ceiling-mounted gas delivering unit 10 includes a gas module 12 which is preferably mounted to the ceiling 14 by an articulatable linkage 16. Since the ceiling mounted gas delivering unit 10 is specifically designed for use in a room having a plurality of ceiling mounted devices, such as a catheter laboratory, the articulatable linkage 16 allows the gas module 12 to be moved easily to a wide variety of locations. Moreover, the gas module 12 is made quite small due to the fact that most catheterization procedures are performed on patients without the use of anesthesia. Therefore, only a few selected gases, such as air, compressed air, oxygen and a vacuum, are delivered to the gas module 12.

Figure 2:
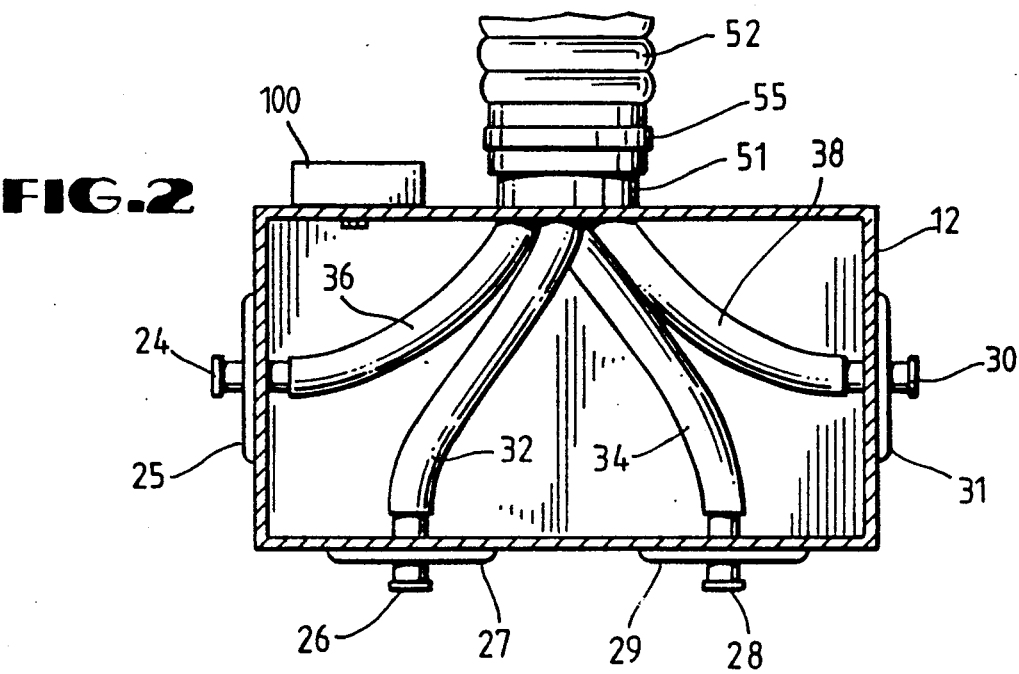
FIG. 2 is a cross-sectional view of a gas module associated with the ceiling-mounted gas delivering unit taken generally along line 2—2 FIG. 1.

The gas module 12 receives these gases from a suitable source, and controllably delivers selected gases to a patient. As shown in FIG. 1, the gas module 12 preferably receives these gases from gas-carrying pipes 18 (20,22,23) which are disposed within the ceilings or walls of the examination room in which the ceiling-mounted gas delivering unit 10 is installed. Referring to FIG. 2, the gas module 12 includes four gas outlets 24,26,28, and 30, each of which is held in place by a suitable cover plate 25,27,29, and 31. As shown, outlets 24 and 26 provide a vacuum for anesthesia scavenging, outlet 28 delivers oxygen, and outlet 30 delivers compressed air. Alternatively, the compressed air outlet 30, which is seldom used in catheterization procedures, may be replaced with a holder (not shown) which is suitable to retain a container into which vacuumed fluids are deposited. The outlets 24,26,28, and 30 preferably include pressure regulating valves or flow regulating valves which help to control the pressure or amount of gas discharged from the outlets, as is known in the art.

Preferably, control valves and gauges (not shown) are attached to at least the oxygen and vacuum outlets 24,26,28 so that an attendant can control the amount of gas or vacuum being delivered to a patient. Since the exact amount of compressed air is not critical, a gauge is preferably not attached to the outlet 30.

Figure 3:
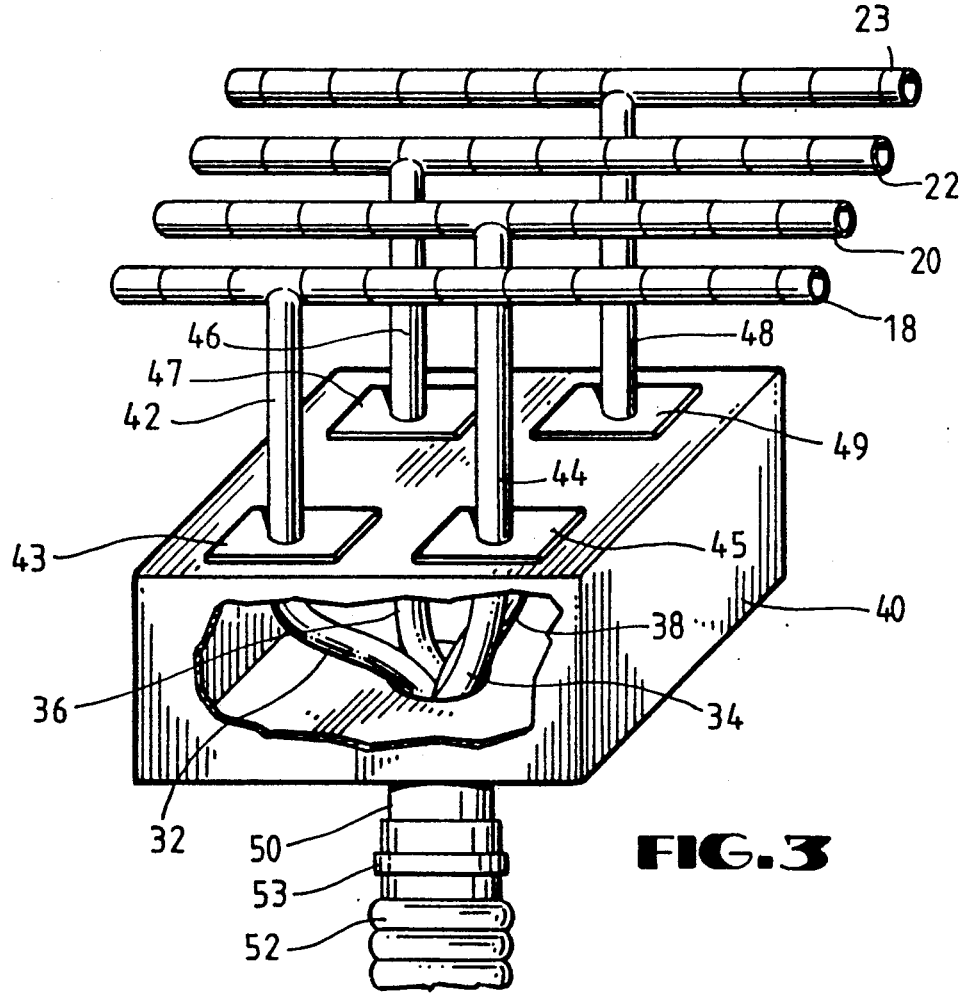
FIG. 3 is a perspective view illustrating a ceiling module which routes gas from gas carrying pipes to the gas delivering unit of the present invention.

The outlets 24,26,28, and 30 receive the gases from the respective pipes 22,18,20, and 23 through respective hoses 36,32,34, and 38, as illustrated in FIG. 3. A ceiling module 40 includes a plurality of connection tubes 42,44,46, and 48 which are connected to the respective gas carrying pipes 18,20,22, and 23 by a suitable means, e.g., by using a T-shaped junction or a perforating, self-sealing clamp. The connection tubes 42,44,46,48 connect to respective outlets 43,45,47,49 in the ceiling module 40. The hoses 32,34,36, and 38 are attached to the respective outlets 43,45,47, and 49 within the ceiling module 40, and are routed through an outlet tube 50, which serves as a passageway between the ceiling 14 and the room. The hoses 32,34,36, and 38 extend between the outlet tube 50 and an inlet tube 51 of the gas module 12 within a conduit 52. The conduit is connected to the outlet tube 50 and the inlet tube 51 by any suitable means, e.g., using band clamps 53,55. The conduit 51 is preferably corrugated to provide flexibility so that it generally extends along the articulatable linkage 16, and the conduit 52 and the hoses 32,34,36, and 38 are preferably made of rubber or of a flexible plastic material. The conduit 52 is secured to the articulatable linkage 16 by a plurality of clamps 54 which hold the conduit 52 onto the articulatable linkage 16 at preselected locations. Since the gas is delivered to the gas module 12 using the flexible conduit 52, instead of by routing the hoses within the linkage member, the articulated linkage 16 is much smaller, slimmer and lighter than commercially available ceiling-mounted gas modules.

The articulatable linkage 16 includes a base 56 which mounts the linkage 16 onto the ceiling 14. A vertical support arm 58 which is connected to the base 56 extends downwardly from the ceiling 14. The lower end of the vertical support arm 58 carries a linkage member 66 which connects a horizontally disposed arm 68 to the vertical support arm 58. The linkage member 66 preferably includes an upwardly extending post 70 (as shown by the phantom lines in FIG. 1), and the arm 68 includes a sleeve member 72 which slides over the post 70. The arm 68 is then secured to the vertical support arm 58 by attaching a cap 73 to top of the post 70. Therefore, the horizontal arm 68 is pivotable about the longitudinal axis 74 of the post 72, and the range of motion of the arm 68 is limited due to the obstruction of the vertical support arm 58, as shown by dashed line 75 in FIG. 4. This limited range of motion prevents the conduit 52 from wrapping around the articulatable linkage 16.

The outer end of the horizontal arm 68 includes a sleeve member 76 through which a post 78 (as shown by phantom lines in FIG. 1) extends. The post 78 is part of a connecting member 80 which connects the horizontal arm 68 to a tilting arm 82. The sleeve member 76 is secured to the connecting member 80 by attaching a cap 88 to the top of the post 78.

Figure 4:
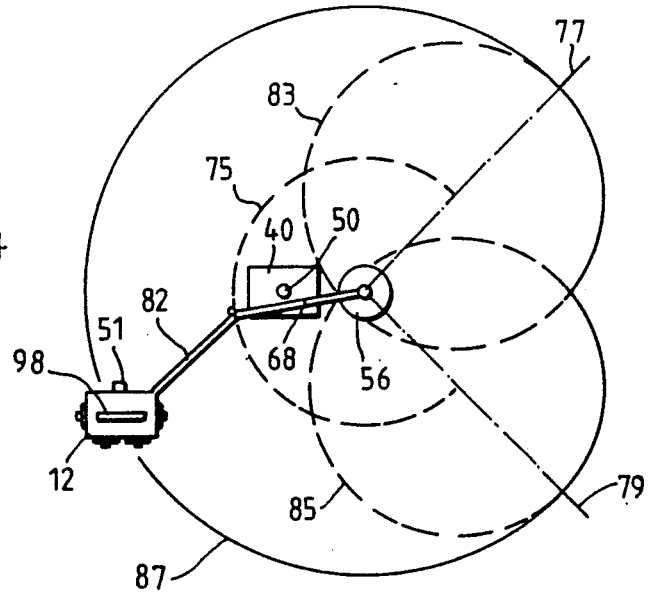
FIG. 4 illustrates a preferred range of motion of the gas delivering unit of FIG. 1.

The connecting member 80 allows the tilting arm 82 to move with two degrees of freedom; the first degree of freedom being about the longitudinal axis 84 of the post 78, and the second being upwardly or downwardly about a spring-loaded joint 86. As illustrated in FIG. 4, at the limits (dashed lines 77 and 79) of the range of motion of the horizontal arm 68, the range of motion of the tilting arm 82 about the longitudinal axis 84 is shown by dashed lines 83,85 to be about 360°. However, the range of motion is advantageously limited to slightly less than 360° to prevent the conduit 52 from wrapping around the articulatable linkage 16.

The outer end of the tilting arm 82 is connected to the gas module 12 via a self-leveling linkage 90. The tilting arm 82 allows the gas module 12 to be moved upwardly or downwardly as shown by the phantom lines in FIG. 1, while the attitude or orientation of the gas module 12 remains relatively unchanged between the upper and lower positions of the tilting arm 82. This is due to the self-leveling linkage 90 which maintains the desired attitude of the gas module 12 through the range of motion of the tilting arm 82. The accuracy of sensitive gauges, such as mercury gauges, which are attached to the outlets, is maintained, since the attitude of the gas module 12 remains relatively unchanged. The self-leveling linkage 90 includes a shaft 92 which connects the control module 12 to the tilting arm 82, and the shaft 92 includes a bearing portion 94 which allows the gas module 12 to rotate about the longitudinal axis 96 of the shaft 92.

The ability of the horizontal arm 68 to pivot about the post 70 and the ability of the tilting arm 82 to pivot about the post 76, allows the gas module 12 to be positioned horizontally anywhere within the region bounded by the solid line 87 (FIG. 4). The vertical positioning of the gas module 12 is determined by the length of the vertical support arm 58, and by the vertical range of motion of the tilting arm 82 about the spring-loaded joint 86. In rooms where a greater vertical range of motion is desirable, the vertical support arm 58 could be adapted to slide axially and, thus, alter the length of the vertical support arm 58.

The movement of the gas module 12 is controlled solely by forces applied to a handle 98 which is preferably connected to the bottom of the control module 12. Because the spring-loaded joint 86 biases the gas module 12 upwardly, the gas module 12 acts as a counterweight to overcome the spring force of the joint 86. Once the gas module 12 is moved into a desired position, the weight of the gas module 12 maintains the desired vertical position of the tilting arm 82. Should the gas module 12 be of an inappropriate weight, however, an additional counterweight 100 or counter-balance may be used to control the vertical positioning of the gas module 12. Preferably, any additional counterweight is attached to the gas module 12.

Overall, the gas delivering unit 10 is lightweight by virtue of the slimness of the support members, i.e., the linkages and arms, which are used to make the articulatable linkage 16. Moreover, the support members are preferably made of a lightweight material, such as aluminum, to further reduce the weight of the gas delivering unit 10. Experimental units have been made using a commercially available articulatable linkage from Burkhart Roentgen Inc., 3 River Rd. South, Cornwall Bridge, Conn. 06754, which is referred to as an "overhead counterpoise". The weight of the articulatable linkage 16 is between about 30 pounds and about 80 pounds (depending on length), the weight of the gas module 12 is between about 20 pounds and about 40 pounds, the weight of the hoses 32,34,36,38 and conduit 52 is between about 10 pounds and about 30 pounds. Therefore, the weight of the entire gas delivering unit 10 is between about 60 pounds and about 150 pounds.

The range of motion and the slim profile of the articulatable linkage 16, allows the gas delivering unit 10 to be mounted onto a ceiling in an examination room having a plurality of devices mounted on the ceiling above a patient, because the articulatable linkage 16 is able to position the gas module 12 near the patient by winding between the other devices in the room.

We claim:
1. A low-bulk gas delivering apparatus for use in a catheter laboratory, comprising:
 a universally articulatable support arm having a first end and a second end, the first end being adapted to mount onto a ceiling;
 a gas module being mounted onto the second end of said support arm for movement therewith, and being adapted to deliver gas; and a hose connecting said gas module to a source of gas, said hose generally extending along said support arm and being disposed outside of said support arm.

2. The apparatus, as set forth in claim 1, wherein said apparatus weighs between 60 pounds and 150 pounds.

3. The apparatus, as set forth in claim 1, further comprising means for maintaining said universally articulatable support arm in a plurality of selected positions.

4. The apparatus, as set forth in claim 1, wherein said gas module comprises at least one outlet being connected to said hose, said outlet being adapted to deliver gas from said hose.

5. The apparatus, as set forth in claim 1, further comprising a handle being attached to said gas module.

6. The apparatus, as set forth in claim 1, further comprising a self-leveling linkage which connects said gas module to the second end of said articulatable support arm, said self-leveling linkage maintaining a selected orientation of said gas module throughout the range of motion of said articulatable support arm.

7. A gas delivering apparatus for use in a catheter laboratory having a ceiling, wherein gas-carrying pipes are disposed above the ceiling, said apparatus comprising:
   a first support arm having a first end and a second end and having a longitudinal axis generally extending from said first end to said second end, said first end being adapted to attach to said ceiling so that said support arm extends downwardly from said ceiling wherein said longitudinal axis is generally perpendicular to said ceiling;
   a second support arm having a first end and a second end, the first end of said second support arm being pivotally connected to the second end of said first support arm to permit said second support arm to pivot generally about the longitudinal axis of said first support arm;
   a third support arm having a first end and a second end, the first end of said third support arm being pivotally connected to the second end of said second support arm to permit the second end of said third support arm to move upwardly toward said ceiling and downwardly away from said ceiling and to permit said third support arm to horizontally pivot about the second end of said second support arm;
   a gas module being connected to the second end of said third support arm; and
   a hose having a first end and a second end, the first end being connected to one of said gas-carrying pipes in said ceiling and the second end being operably connected to said gas module to deliver gas to said gas module.

8. The apparatus, as set forth in claim 7, wherein said apparatus weighs between 60 pounds and 150 pounds.

9. The apparatus, as set forth in claim 7, wherein the first end of said third support arm comprises a spring-loaded joint which biases the second end of said third support arm upwardly.

10. The apparatus, as set forth in claim 9, wherein said gas module comprises a counter-weight which opposes the upward bias of said spring-loaded joint.

11. The apparatus, as set forth in claim 10, wherein the weight of said gas module substantially cancels the upward bias of said spring-loaded joint so that said gas module maintains a selected vertical position.

12. The apparatus, as set forth in claim 9, further comprising a counter-weight being attached to said gas module for opposing the upward bias of said spring-loaded joint.

13. The apparatus, as set forth in claim 12, wherein the combined weight of said counter-weight and said gas module substantially cancels the upward bias of said spring-loaded joint so that said gas module maintains a selected vertical position.

14. The apparatus, as set forth in claim 7, further comprising a self-leveling linkage which connects said gas module to the second end of said third support arm, said self-leveling linkage maintaining a selected orientation of said gas module throughout the range of motion of said third support arm.

15. The apparatus, as set forth in claim 7, wherein said gas module comprises at least one outlet being connected to said hose, said outlet being adapted to deliver gas from said hose.

16. The apparatus, as set forth in claim 15, further comprising a plurality of hoses, each hose having a first end and a second end, the first end of each hose being connected to a respective one of said gas-carrying pipes in said ceiling and the second end of each hose being operably connected to said gas module to deliver gas to said gas module, said hoses being disposed outside of said first, second, and third support arms.

17. The apparatus, as set forth in claim 16, wherein said gas module comprises a plurality of outlets, each outlet being connected to one of said respective hoses, each of said outlets being adapted to deliver gas from said respective hoses.

18. The apparatus, as set forth in claim 7, further comprising a handle being attached to said gas module.

19. A ceiling-mounted gas delivering apparatus for use in a catheter laboratory, said apparatus comprising: an articulatable support member, comprising:
   a first support arm having a first end and a second end and having a longitudinal axis generally extending from said first end to said second end, said first end being adapted to attach to a ceiling so that said support arm extends downwardly from said ceiling wherein said longitudinal axis is generally perpendicular to said ceiling;
   a second support arm having a first end and a second end, the first end of said second support arm being pivotally connected to the second end of said first support arm to permit said second support arm to pivot horizontally about said first support arm;
   a third support arm having a first end and a second end, the first end of said third support arm being pivotally connected to the second end of said second support arm to permit the second end of said third support arm to move vertically upwardly toward said ceiling and downwardly away from said ceiling and to permit said third support arm to pivot horizontally about the second end of said second support arm;
   a gas module being rotatably mounted onto the second end of said third support arm; and
   a hose connecting said gas module to a source of gas, said hose being disposed outside of said support member.

20. The apparatus, as set forth in claim 19, wherein said apparatus weighs between 60 pounds and 150 pounds.

21. The apparatus, as set forth in claim 19, further comprising means for maintaining said articulatable support member in a plurality of selected positions.

22. The apparatus, as set forth in claim 19, further comprising a self-leveling linkage which connects said gas module to the second end of said third support arm, said self-leveling linkage maintaining a selected orientation of said gas module throughout the range of motion of said articulatable support member.

23. The apparatus, as set forth in claim 21, wherein said maintaining means comprises a spring-loaded joint connected to the first end of said third support arm to bias the second end of said third support arm upwardly.

24. The apparatus, as set forth in claim 23, wherein said gas module comprises a counter-weight which opposes the upward bias of said spring-loaded joint.

25. The apparatus, as set forth in claim 24, wherein the weight of said gas module substantially cancels the upward bias of said spring-loaded joint so that said gas module maintains a selected vertical position.

26. The apparatus, as set forth in claim 23, further comprising a counter-weight being attached to said gas module for opposing the upward bias of said spring-loaded joint.

27. The apparatus, as set forth in claim 26, wherein the combined weight of said counter-weight and said gas module substantially cancels the upward bias of said spring-loaded joint so that said gas module maintains a selected vertical position.

28. The apparatus, as set forth in claim 19, wherein said gas module comprises at least one outlet being connected to said hose, said outlet being adapted to deliver gas from said hose.

29. The apparatus, as set forth in claim 28, further comprising a plurality of hoses, each of said hoses connecting said gas module to a source of gas, and each of said hose generally extending along said support member and being disposed outside of said support member.

30. The apparatus, as set forth in claim 29, wherein said gas module comprises a plurality of outlets, each outlet being connected to one of said respective hoses, each of said outlets being adapted to deliver gas from said respective hoses.

31. The apparatus, as set forth in claim 7, further comprising a handle being attached to said gas module.

32. A ceiling-mounted gas delivering apparatus for use in a catheter laboratory, said apparatus comprising:
 a first support arm having a first end and a second end, said first end being adapted to attach to a ceiling so that said support arm extends downwardly from said ceiling;
 a second support arm having a first end and a second end;
 a first pivotable linkage connecting the second end of said first support arm to the first end of said second support arm, said first pivotable linkage permitting said second support arm to pivot about the second end of said first support arm;
 a third support arm having a first end and a second end;
 a second pivotable linkage connecting the second end of said second support arm to the first end of said third support arm, said second pivotable linkage permitting the second end of said third support arm to universally pivot about the second end of said second support arm;
 a gas module having at least one outlet for delivering gas;
 a third pivotable linkage connecting the second end of said third support arm to said gas module, said third pivotable linkage maintaining a preselected orientation of said gas module throughout the range of motion of said support arms; and
 at least one tube connecting said outlet of said gas module to a source of gas, said tube generally extending along said support arms and being disposed outside of said support arms.

33. The apparatus, as set forth in claim 32, wherein said apparatus weighs between 60 pounds and 150 pounds.

34. The apparatus, as set forth in claim 32, wherein said second pivotable linkage comprises a spring-loaded joint which biases the second end of said third support arm upwardly.

35. The apparatus, as set forth in claim 34, wherein said gas module comprises a counter-weight which opposes the upward bias of said spring-loaded joint.

36. The apparatus, as set forth in claim 35, wherein the weight of said gas module substantially cancels the upward bias of said spring-loaded joint so that said gas module maintains a selected vertical position.

37. The apparatus, as set forth in claim 34, further comprising a counter-weight being attached to said gas module for opposing the upward bias of said spring-loaded joint.

38. The apparatus, as set forth in claim 37, wherein the combined weight of said counter-weight and said gas module substantially cancels the upward bias of said spring-loaded joint so that said gas module maintains a selected vertical position.

39. The apparatus, as set forth in claim 32, wherein said gas module comprises a plurality of outlets for delivering gas.

40. The apparatus, as set forth in claim 39, further comprising a plurality of hoses, each of said hoses connecting to a respective outlet of said gas module, and each of said hose generally extending along said support member and being disposed outside of said support member.

41. The apparatus, as set forth in claim 32, further comprising a handle being attached to said gas module.

* * * * *